United States Patent [19]

Niu et al.

[11] Patent Number: 5,869,676

[45] Date of Patent: Feb. 9, 1999

[54] PROCESS FOR THE SYNTHESIS OF RIBONUCLEOTIDE REDUCTASE INHIBITORS 3-AP AND 3-AMP

[75] Inventors: ChuanSheng Niu, Cheshire; Jun Li, Hamden; Xiuyan Li, New Haven; Terrence W. Doyle, Killingworth; Shu-Hui Chen, Hamden, all of Conn.

[73] Assignee: Vion Pharmaceuticals, Inc., New Haven, Conn.

[21] Appl. No.: 856,559

[22] Filed: May 15, 1997

[51] Int. Cl.[6] ............... C07D 213/73; C07D 213/75; C07D 213/61; C07D 213/55

[52] U.S. Cl. ............... 546/310; 546/309; 546/318

[58] Field of Search ................... 546/309, 310, 546/318

[56] References Cited

PUBLICATIONS

Hoye, et al., "Studies of Palladium–Catalyzed Cross–Coupling Reactions for Preparation of Highly Hindered Biaryls Relevant to the Korupensamine/Michellamine Problem," J. Org. Chem., vol. 61, No. 22, 1996, pp. 7940–7942.

Zhou, et al., "Synthesis of β–Mono–, Tetra–, and Octasubstituted Sterically Bulky Porphyrins via Suzuki Cross Coupling," J. Org. Chem., vol. 61, No. 11, 1996, pp. 3590–3593.

Liu, et al., "Synthesis and Antitumor Activity of Amino Derivatives of Pyridine–2–carboxaldehyde Thiosemicarbazone," Journal of Medicinal Chemistry, vol. 35, No. 20, 1992, pp. 3672–3677.

*Primary Examiner*—Bernard Dentz
*Attorney, Agent, or Firm*—Henry D. Coleman; R. Neil Sudol

[57] ABSTRACT

The present invention relates to improved, efficient chemical syntheses of 3-aminopyridine-2-carboxaldehyde thiosemicarbazone (3-AP) and 3-amino-4-methylpyridine-2-carboxaldehyde thiosemicarbazone (3-AMP).

12 Claims, 3 Drawing Sheets

Route A: via 2-Methyl-3-nitropyridine

Route B: via 2-Vinyl-3-nitropyridine

Route C: via 2-Vinyl-3-aminopyridine

Overall yield = 64%

PROCESS FOR THE SYNTHESIS OF RIBONUCLEOTIDE REDUCTASE INHIBITORS 3-AP AND 3-AMP

FIELD OF THE INVENTION

The present invention relates to novel chemical syntheses of ribonucleotide reductase inhibitors.

BACKGROUND OF THE INVENTION

Cancer is one of the leading causes of death known today, and effective treatment of many solid tumors still remains elusive. It is believed that novel antitumor drugs possessing a strong inhibitory effect on ribonucleotide reductase, an essential enzyme for cellular replication would be a useful addition to present drug regimens for treating cancer.

It is well-known that the reductive conversion of ribonucleotides to the corresponding deoxyribonucleotides is a key step in the biosynthesis of DNA. Since deoxyribonucleotides are present in extremely low levels in mammalian cells, investigators have assumed that an inhibitor of ribonucleotide reductase could be more effective than an inhibitor of DNA polymerase in blocking DNA synthesis. See, Cory and Chiba, "Combination Chemotherapy Directed at the Components of Nucleoside Diphosphate Reductase", *Inhibitors of Ribonucleoside diphosphate reductase Activity*, Cory, J. G. and Cory, A. M. Eds.; Pergamon Press: Oxford, 1989; pp 245–264. Consequently, through this work it was believed that the development of strong inhibitors of ribonucleotide reductase would create potential powerful weapons against cancer.

For many years, studies of novel α-(N)-heterocyclic carboxaldehyde thiosemicarbazones (HCTs), a class of the most potent inhibitors of ribonucleoside diphosphate reductase, has attracted considerable interest. A variety of HCTs such as 5-hydroxypyridine-2-carboxaldehyde thiosemicarbazone (5 HP), 4-methyl-5-amino-1-formylisoquinoline thiosemicarbazone (MAIQ-1), 5-(acetylamino)pyridine-2-carboxaldehyde thiosemicarbazone (5-AAP), 3- and 5-aminopyridine-2-carboxaldehyde thiosemicarbazone (3-AP and 5-AP) and their 4-methyl derivatives (3-AMP and 5-AMP), 3- and 5-hydroxy-4-methylpyridine-2-carboxaldehyde thiosemicarbazone (3-HMP and 5-HMP) have been reported. See, DeConti, et al., *Cancer Res.*, 1972, 32, 1455–1462; Agrawal, et al., *J. Med. Chem.* 1976, 19, 970–972; French, et al., *J. Med. Chem.*, 1974, 17, 172–181; Liu, et al., *J. Med. Chem.* 1992, 35, 3672–3677; Wang, et al., *J. Med. Chem.* 1992, 35, 3667–3671.

Structure-activity relationship studies of a series of HCTs revealed that both 3-AP and 3-AMP showed much better therapeutic effects against L1210 leukemia, M-109 lung carcinoma and A2780 human ovarian carcinoma than other HCTs reported to date. Liu, et al., *J. Med. Chem.* 1992, 35, 3672–3677; Agrawal, et al., "The Chemistry and Biological Activity of the α-(N)-Heterocyclic Carboxaldehyde Thiosemicarbazones." *Progress in Medicinal Chemistry*; Ellis, G. P.; West, G. B., Eds.; Elsevier/North-Holland Biomedical Press: New York, 1978; Vol. 15, pp 321–356. In addition, 3-AP and 3-AMP are potent agents with significant antineoplastic activity in comparison with hydroxyurea (HU), an approved ribonucleotide reductase inhibitor used in clinics. The study of these compounds on a much larger scale has necessitated scale-up production of these agents.

As outlined in FIG. 1, the first syntheses of 3-AP and 3-AMP were accomplished in Dr. Alan Sartorelli's laboratories at Yale University. Although the previous synthesis has the advantage of low cost of the materials used in the synthetic procedure, the scheme has proved to be troublesome due to long reaction sequences, low yields and difficult handling. For this reason, the present inventors investigated the synthesis and have developed new methods to prepare 3-AP and 3-AMP.

OBJECTS OF THE INVENTION

It is an object of the invention to provide efficient chemical syntheses for 3-aminopyridine-2-carboxyaldehyde thiosemicarbazone (3-AP) and 3-amino-4-methylpyridine-2-carboxaldehyde thiosemicarbazone (3-AMP).

BRIEF DESCRIPTION OF THE INVENTION

The present invention relates to improved, efficient chemical syntheses of 3-aminopyridine-2-carboxaldehyde thiosemicarbazone (3-AP) and 3-amino-4-methylpyridine-2-carboxaldehyde thiosemicarbazone (3-AMP).

In the present invention, an efficient synthesis of 3-AP and 3-AMP is provided. In this method of the present invention, the target chemotherapeutic agents are synthesized from readily available starting materials in total yields of greater than 30%. This is in comparison to total yields of less than about 10% using alternative synthetic methods of the prior art.

In the present invention which relates to novel syntheses of 3-AP and 3-AMP, a particularly key step is a Stille or Heck vinylation reaction which occurs at the C-2 position of a pyridine moiety to produce a 2-vinyl pyridine intermediate in high yield (often as much as 70+%), which can be readily converted in a series of high yield synthetic steps to 3-AP or 3-AMP, respectively. In this method, pyridine moiety P, below, is converted to the 2-vinyl derivative 2-VP using a Heck or Stille vinylation reaction as shown in scheme 2.

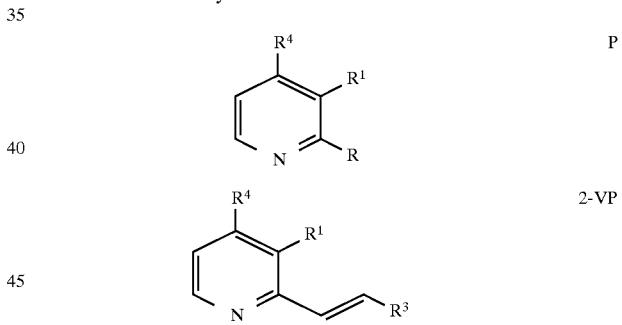

where

R is Cl, Br, I, OMs, OTf or OTs;

$R^1$ is $NO_2$, $NH_2$, NHP, NPP', $N_3$ or $CO_2R^2$;

P and P' are protecting groups;

$R^2$ is Me, Et, Pr or i-Pr; and $R^3$ is H, $C_1$ to $C_{20}$ alkyl, aryl, substituted aryl or CO $R^2$; and $R^4$ is H or $CH_3$.

Protecting groups which may be used as P and P', include ester groups such as

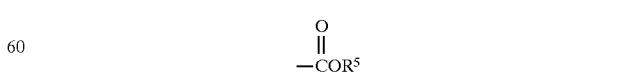

where $R^5$ is an alkyl group, such as methyl, ethyl, propyl, I-propyl, butyl and t-butyl, phenyl, substituted phenyl, benzyl, and substituted benzyl, among numerous others. Other amino-protecting groups which are well known in the art may also be used.

The 2-vinylation reaction takes place preferably using a reagent selected from among the following: $Bu_3SnCH=CHR^3$, $(OH)_2B-CH=CHR^3$, $ClZnCH=CHR^3$ and $XMgCH=CHR^3$ (a grignard reagent, where X is a halide such as I, Br, Cl, among others). The vinylation reaction takes place in the presence of triphenylphosphine ($PPh_3$) and/or tetrakis(triphenylphosphine) palladium [$Pd(PPh_3)_4$] usually in a solvent such as toluene, xylene or another organic solvent in the presence of heat. Upon introduction of the vinyl group at the C-2 position of the pyridine, the group can thereafter be converted to an aldehyde (by ozonolysis or an equivalent process), which can be subsequently converted to a carboxaldehyde thiosemicarbazone in preparation of 3-AP or 3-AMP. In an alternative vinylation reaction, the use of styrene, 3-methylpropenoate or related vinylation reagents in combination with palladium acetate [$Pd(OAc)_2$] and triphenyl phosphine ($PPh_3$) will introduce a vinyl group at the C-2 position of the pyridine moiety which can be converted readily to the 2-carboxaldehyde and eventually the carboxaldehyde semicarbazone or hydrazone.

Other important aspects of the present invention include improvements over the prior art synthesis. In the prior art, the conversion of a 2-chlorine pyrimidine derivative to a 2-methyl pyrimidine derivative is a two step process having a combined yield of only 60%. In the instant invention this conversion is performed in a single step with a yield of approximately 90%. By performing this methylation under Suzuki conditions, the instant invention, in addition to reducing the number of steps required for the synthesis and improving overall yield, also makes handling easier and therefore makes commercial large-scale production easier. The high yield of this reaction is an unexpected result.

Furthermore, where the prior art requires the difficult conversion of the 2-carboxaldehyde into an acetal and reduction of the nitro group at position 3 before the coupling of the thiosemicarbazide at the 2-position, the present inventors have discovered a shorter and more efficient process in which the 2-carboxaldehyde is directly coupled to the thiosemicarbazide, followed by simple reduction of the nitro group.

In preferred aspects according to the present invention, the present processes have the advantage of allowing the preparation of large quantities of 3-AP or 3-AMP without using expensive starting materials and providing final product in high overall yield. The processes of this invention produce high purity anti-cancer compounds in yields amenable to scale-up and commercial preparation. The present methods address the relatively low yields of the prior art methods and make commercialization of 3-AP and 3-AMP economically viable.

DETAILED DESCRIPTION OF THE INVENTION

The term "neoplasia" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascitic and solid tumors.

The term "protected" is used to refer to a phosphate group or hydroxyl group in any one or more of the intermediates which is protected from undesired reactions, but which protection may be removed under selective conditions. Protection groups which may be used for this purpose include, for example, trichloroethyl, ethyl, cyanoethyl, trimethylsilylethyl, silylethyl, t-butyldimethylsilyl, t-butyl, triphenylsilyl and t-butyldiphenylsilyl, among numerous others including ester groups, such as methyl, ethyl, propyl, i-propyl, butyl and t-butyl esters, among others. The blocking groups may be broadly chosen from the class of silyl blocking groups, ether blocking groups and ester blocking groups, each blocking group being chosen for its ability to protect a moiety from an undesirable reaction taking place and its ease of removal and compatibility of chemistry.

Figure 1:
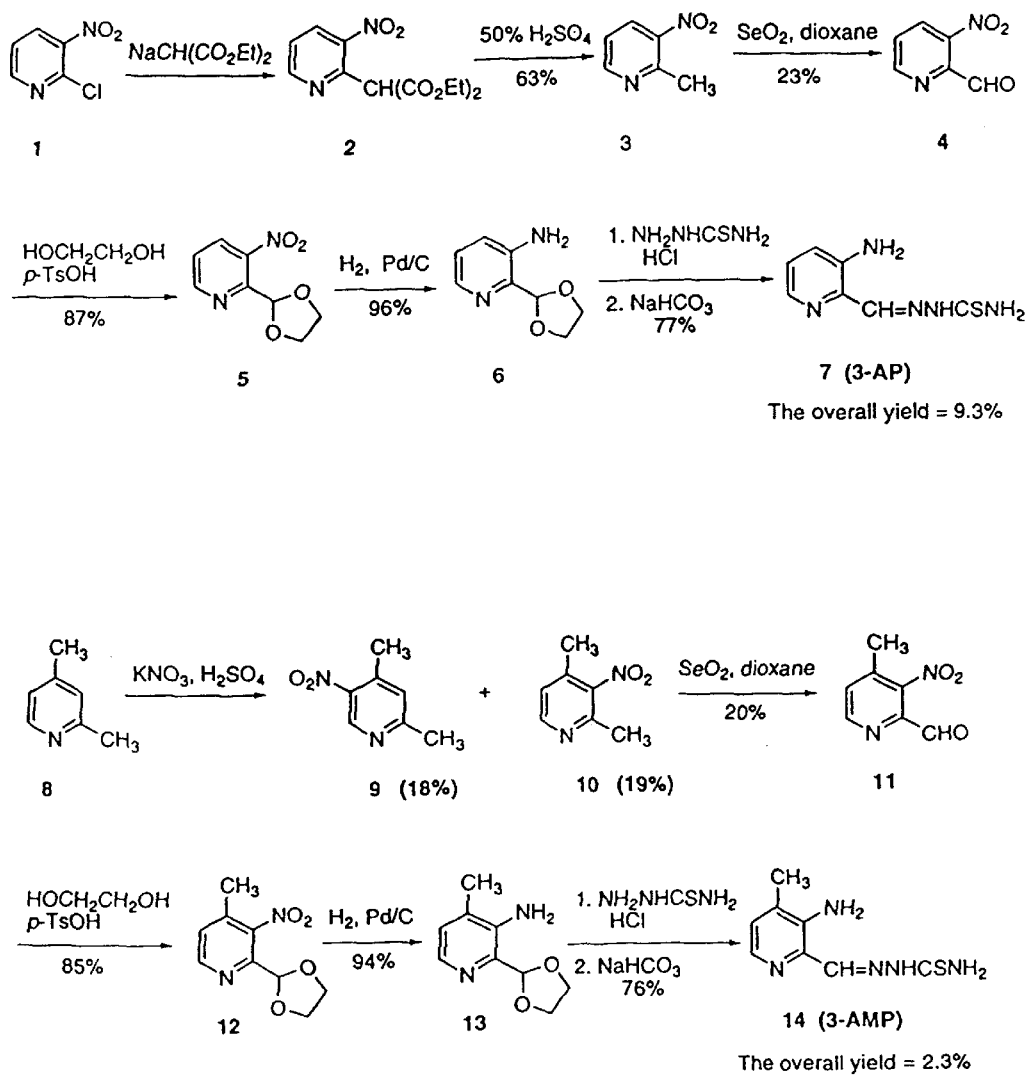
FIG. 1, Scheme 1 represents the prior art synthesis of 3-AP and 3-AMP, each proceeding through a pyridine 2-carboxaldehyde intermediate (4 and 11). In the case of 3-AP, the synthesis proceeds to completion in a total yield of about 9.3%. In the case of 3-AMP, the synthesis proceeds to completion in a total yield of about 2.3%.
Figure 2:
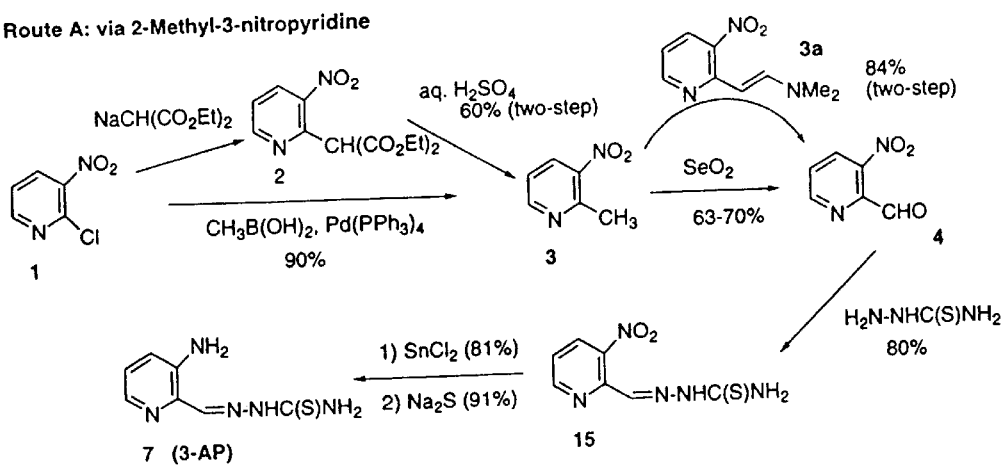
FIG. 2, Scheme 2 provides two novel syntheses of 3-AP from 2-chloro-3-nitropyridine 1 and a novel synthesis from 2-chloro-3-aminopyridine 19. These syntheses proceed to completion in total yields ranging from 31.5% to 68.4%. In fact, the chemistry described in route C has been used to produce 3-AP in greater than 20 g. quantity in a single operation.
Figure 2:
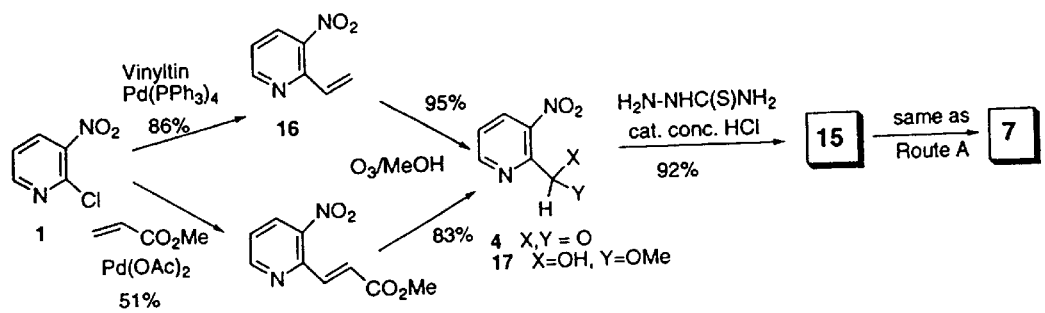
Figure 2:
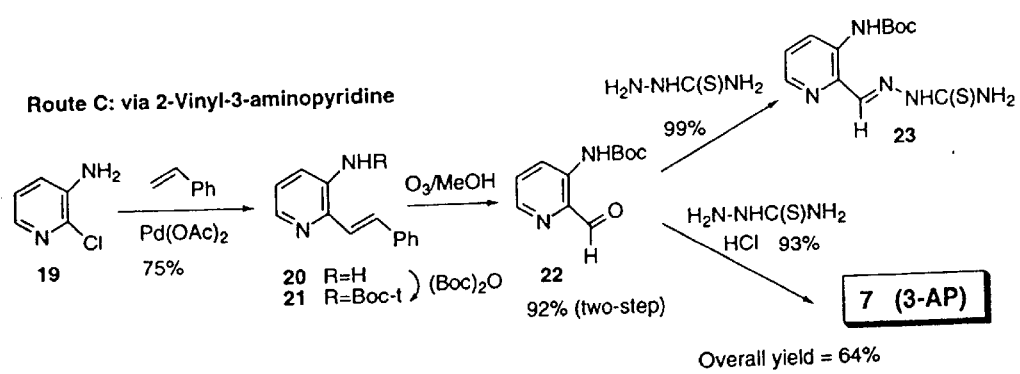

The improved syntheses of 3-AP and 3-AMP of the present invention, having higher yields and being safer and more easily performed, are outlined in Schemes 2 and 3, respectively. Three synthetic routes were developed for the synthesis of 3-AP as set forth in FIG. 2. Advantageously, the number of steps in the prior art procedure (see FIG. 1, Scheme 1), was reduced by elimination of the acetal protection and deprotection steps of the prior art synthesis. In Routes A and B, as set forth in Scheme 2, 2-Carboxaldehyde 4 was directly converted to hydrazone 15 and subsequent reduction of the nitro functional group to the amine was effected using either stannous chloride (see Atwal, K. S., et al.; *J. Med Chem* 1996, 39, 305–313 for a description of this type of reaction) or sodium sulfide (Zinin reduction, see Porter, H. K., *Org React* 1973, 20, 455–483). In Route C, N-Boc protected 2-carboxaldehyde 22 was directly coupled with thiosemicarbazide and simultaneously deprotected to produce 3-AP. These general approaches provided 3-AP in good yields.

Three different approaches are shown in Scheme 2 to synthesize the 2-carboxaldehyde pyridine intermediates (compounds 4 and 22). In the first of the three approaches set forth in Route A, methylation of the 2-chloro pyridine compound 1 followed by oxidation of the 2-methyl group with selenium dioxide provided the 2-carboxaldehyde compound 4, which is readily converted to 3-AP in two high-yield steps. In an alternative approach shown as a branch of Route A, 2-methyl-3-nitropyridine 3 is reacted with dimethylformamidedimethylacetal (DMFDMA, although any number of related acetal analogs of DMFDMA may be used in this reaction) to produce intermediate 3a, followed by oxidation with sodium periodate ($NaIO_4$) provides aldehyde 4 in 84% overall yield, a significant improvment over the oxidation procedure of 2-methyl-3-nitropyridine 3 with selenium dioxide to produce aldehyde 4. The complete synthesis of 3-AP from 2-chloro-3-nitropyridine 1 may be obtained in 55% total yield.

In an alternative procedure shown as the upper branch of Route B, introduction of the 2-vinyl group using a palladium mediated Stille vinylation reaction as the key step (see Attwood, M. R., et al., *Tetrahedron Lett,* 1996, 37, 2731; Skoda-Foldes, R, et al., *Tetrahedron Lett,* 1996, 37, 2085; and Subramanyam, C., et al., *Tetrahedron Lett,* 1996, 37, 459) followed by ozonolysis gave the 2-carboxaldehyde compound 4 in very high yield. The third method, shown in Route C and the lower branch of Route B, employed a palladium mediated Heck vinylation reaction (see Sit, S. Y., et al., *Bioorg Med Chem Lett,* 1996, 6, 499; and Ojima, I., et al., *Chem Rev,* 1996, 96, 635–662 for descriptions of this type of reaction) followed by ozonolysis to form carboxaldehyde compounds 4 or 22 (where R is protective group for the 3-amino position including a Boc-t group, an ester group, or related blocking group which is readily known in the art and is consistent with the chemistry employed in this reaction sequence), which is readily converted to 3-AP using thiosemicarbazide followed by conditions (for example, acid) to remove the amino protecting group or directly with thiosemicarbazide in HCl. The yield of 3-AP from each of the three alternative synthesis pathways is between three and seven times the yield of the prior art synthesis, an unexpectedly advantageous result. This represents a great advantage in the industrial scale-up of production of 3-AP for clinical trials and ultimately for therapeutic use.

Figure 3:
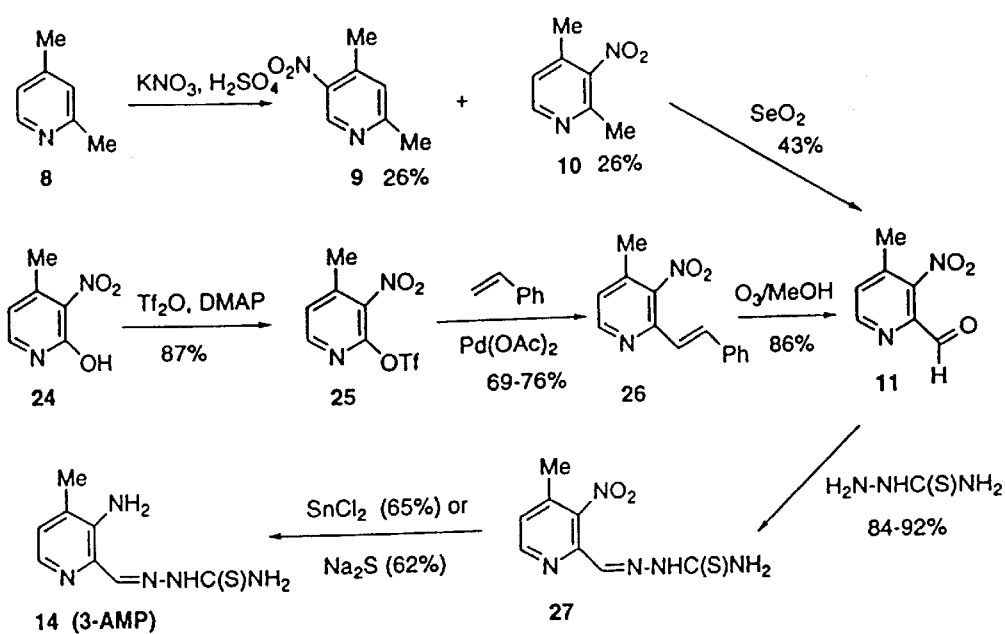
FIG. 3, Scheme 3, provides two novel syntheses of 3-AMP, through intermediate 2-carboxaldehyde 11. These syntheses proceed to completion in total yields ranging from 5.8% to 34%.

Two efficient synthetic pathways for 3-AMP are presented in FIG. 3. As illustrated in FIG. 3, synthesis beginning with dimethyl pyridine 8 reduced the number of steps in the original synthesis and increased the overall yield. Nitrosating the dimethyl pyridine 8 followed by oxidation of the 2-methyl group produced the 2-carboxaldehyde 11, which was directly coupled to thiosemicarbazide to produce the 2-thiosemicarbazone 27 in high yield. The 2-thiosemicarbazone 27 was finally converted to 3-AMP either under Zinin reduction conditions or using stannous chloride, resulting in a yield approximately three times that of the prior art synthesis of 3-AP. The synthesis beginning with substituted pyridine analog 24 provided a more efficient synthesis of the 2-carboxaldehyde 11 by using a high-yielding Stille vinylation reaction after the 2-hydroxyl group of pyridine analog 24 was converted to the 2-OTf group. Ozonolysis of the 2-vinyl group produced the 2-carboxaldehyde 11 in high yield. 2-Carboxaldehyde 11 was reacted with thiosemicarbazide to produce the thiosemicarbazone 27 in high yield which was reduced to 3-AMP using either Zinin reduction conditions or stannous chloride to complete the synthesis. The synthetic route involving Stille vinylation to produce the key intermediate 11 avoided the difficult nitration reaction and oxidation of the 2-methyl group and improved the overall yield an unexpectedly large 15 fold over the prior art preparation of 3-AMP.

While the preferred synthetic chemical method has been described above, one of ordinary skill in the art will recognize that substitute or equivalent steps may be used to obtain the same results. For example, one of ordinary skill may readily substitute for certain of the reagents and virtually all of the solvents used to produce an intermediate as set forth in the various schemes. Formation of 2-vinyl pyridine intermediates, for example, may be readily formed using any appropriate vinyl-forming reagent or reagent combination (including triphenylphosphine or tetrakistriphenylphosphine palladium, as appropriate) and any appropriate solvent. Oxidizing agents for converting vinyl groups or benzyl (methyl) groups to aldehydes (at the 2-position of the pyridine moiety) include selenium dioxide and ozone, but other appropriate oxidizing agents may also be used. In the case of hydrogenolysis, (for example, of the 3-nitro group to a 3-amino group), the use of $SnCl_2$ or $Na_2S$ may be appropriate. One of ordinary skill in the art will be able to readily substitute the use of one protecting group with another protecting group consistent with the overall chemistry to be employed in a synthesis.

Particularly key to an efficient synthesis of 3-AP or 3-AMP is the high-yield introduction of a methyl or vinyl group, preferably vinyl, at the 2 position of the pyridine moiety utilizing a Heck or Stille vinylation reaction or a methylation reaction under Suzuki conditions. These reactions proceed at the 2-position of a pyridine moiety in high yield (generally, greater than 50% and in most instances, greater than 70%). The advantage of the vinylation reaction is that the 2-vinyl group may be readily converted to a 2-carboxaldehyde group for further conversion to the 2-thiosemicarbazone using a high yield ozonolysis reaction conducted in a polar solvent, such as methanol. The preferred vinylation reaction is a Heck or Stille vinylation reaction performed utilizing a reagent selected from among the following: $Bu_3SnCH=CHR^3$, $(OH)_2B-CH=CHR^3$, $ClZnCH=CHR^3$ and $XMgCH=CHR^3$. The vinylation reaction takes place in the presence of triphenylphosphine ($PPh_3$) and/or tetrakis(triphenylphosphine) palladium [Pd$(PPh_3)_4$] usually in a solvent such as toluene in the presence of heat. The advantages of the methylation reaction under Suzuki conditions over the two step methylation of the prior art include a greatly improved yield, reduction in the number of steps and therefore handling required and ease in scaling the synthesis up for commercial production. Alternatively, to introduce a vinyl group at the 2-position of 3-nitropyridine, one may advantageously react 2-methyl-3-nitropyridine with dimethylforamamidedimethylacetal (DMFDMA) to produce 2-dimethylamino vinyl-3-nitropyridine compound 3a, followed by oxidation with sodium periodate ($NaIO_4$) to produce carboxaldehyde 4 in an unexpectedly high 84% yield.

Upon introduction of the methyl or vinyl group at the C-2 position of the pyridine, the group can be converted to an aldehyde, which will ultimately be converted to a carboxaldehyde thiosemicarbazone. Where the prior art requires the difficult conversion of the 2-carboxaldehyde into an acetal and reduction of the nitro group at position 3 before the coupling of the thiosemicarbazide at the 2-position, the present method is a shorter and more efficient process in which the 2-carboxaldehyde is directly coupled to the thiosemicarbazide, followed by simple reduction of the nitro group. Reduction of the 3-nitro group in the synthetic pathway is easily performed utilizing standard reduction conditions ($SnCl_2$ or $Na_2S$, among other reduction methods). The synthesis of 3-AP or 3-AMP according to the present invention is completed in a unexpectedly high yield of at least 30% from the readily available starting materials. In certain embodiments, the yield may be as high as 55% or more.

The present invention is now described, purely by way of illustration, in the following examples. It will be understood by one of ordinary skill in the art that these examples are in no way limiting and that variations of detail can be made without departing from the spirit and scope of the present invention.

EXAMPLES

The detailed reaction conditions and characterizations of each compound in the following procedures are provided in this section. All NMR spectra were measured at 300 MHz for 1 H and at 75 MHz for 13 C on QE Plus 300 MHz NMR spectrometer. MS spectra were recorded on VG ZAB-SE mass spectrometer and a VG 70-SE-4F instrument. Some relevant references are also included herein. All solvents were distilled prior to use.

Synthesis of Compound 3 (2-Methyl-3-nitropyridine) (3)

Method 1

Into a flask containing diethyl malonate (20 g, 0.125 mol) was added sodium (2.0 g, 0.087 mol). The reaction mixture was stirred for 1 h at room temperature and then allowed to warm to 120° C. (oil bath temperature) for 50 min. To this yellow suspension of the solid mass was added toluene (120 mL) followed by addition of a solution of 2-chloro-3-nitropyridine 1 (12.8 g, 0.08 mol) in 40 mL of toluene. The reaction mixture was refluxed for 8 h, and then stirred overnight at room temperature. The solvent was removed under reduced pressure and the residue was dissolved in 30% $H_2SO_4$ (60 mL). This reaction mixture was heated to 125° C. (oil bath) for 7 h, cooled and poured into ice (200 g). The reaction mixture was neutralized with saturated NaHCO3 solution, filtered through Celite, extracted several times with ether. The combined extracts were dried over anhydrous Na2SO4. The solvent was evaporated and the residue was distilled under reduced pressure to provide 6.65 g (60%) of the desired product 3.

Method 2

A mixture of 2-chloro-3-nitropyridine 1 (793 mg, 5.0 mmol), methylboronic acid (329 mg, 5.5 mmol), $Pd(PPh_3)_4$ (578 mg, 0.5 mmol) and $K_2CO_3$ (2.073 g, 15.0 mmol) in dioxane (25 mL) was refluxed for 2 days. It was then cooled to room temperature and filtered. The solvent was removed and the residue was isolated by flash chromatography (50% ethyl acetate in hexanes) to provide 623 mg (90%) of 2-methyl-3-nitropyridine 3.

$^1$H NMR (CDCl$_3$) δ 2.88 (s, 3H), 7.36 (dd, 1H, J=4.8 & 8.4 Hz), 8.28 (dd, 1H, J=1.2 & 8.1 Hz), 8.73 (dd, 1H, J=1.2 & 4.8 Hz).

Synthesis of 2-Carboxaldehyde Compound (4)

To a solution of 2-methyl-3-nitropyridine 3 (2.07 g, 0.015 mol) in 35 mL of dioxane was added selenium dioxide (1.88 g, 0.017 mol). The reaction mixture was refluxed for 16 h, then cooled to room temperature and filtered. The solvent was removed under reduced pressure and the residue was purified by flash chromatography on silica gel (hexanes-EtOAc=1:1) to give 1.60 g (70%) of the desired aldehyde 4.

$^1$H NMR (CDCl$_3$) δ 7.71 ( d, 1H, J=4.8 & 8.2 Hz), 8.29 (dd, 1H, J=1.1 & 8.0 Hz), 9.01 (d, 1H, J=1.1 & 4.5 Hz), 10.31 (s, 1H).

Alternative Synthesis of 2-Carboxaldehyde Compound (4)

A solution of 2-Methyl-3-nitropyridine) (3) (276 mg, 2 mmol) and dimethylformamidedimethylacetal (DMFDMA) (477 mg, 4 mmol) in dimethyl formamide (DMF) (1 ml) was heated at 140° C. under $N_2$ for 7 hours, then stirred overnight at room temperature. The solvent was removed under reduced pressure and the residue was dried under vacuum. The reaction was quite clean and gave only one product, the 2-dimethylaminovinyl-3nitropyridine compound 3a, which was used in the next oxidation step without further purification. A soltuion of 3a prepared above and NaIO$_4$ (1.283 g, 6 mmol) in 50% aqueous THF (20 mL) was stirred at room temperature for 2 hours, filtered and extracted with CH$_2$Cl$_2$ several times. The combined extracts were washed with brine and dried over anhydrous Na$_2$SO$_4$. Isolation by flash chromatography on silica gel (hexanes-EtOAc=1:1) gave 256 mg (84%) of 2-carboxaldehyde (4).

Synthesis of Hydrazone Compound (15) from -2-Carboxaldehyde (4)

A mixture of carboxaldehyde 4 (750 mg, 4.93 mmol) and thiosemicarbazide (540 mg, 5.92 mmol) in 70% ethanol (25 mL) was stirred at room temperature for 6 h, filtered and washed with H$_2$O, C$_2$H$_5$OH, ether and dried in vacuo to give 893 mg (80%) of the desired hydrazone 15.

$^1$H NMR (DMSO-d$_6$) δ7.09 (br, 1H), 7.67 (dd, 1H, J=4.9 and 8.2 Hz), 8.27 (s, 1H), 8.38 (d, 1H, J=7.7 Hz), 8.60 (br, 1H), 8.85 (d, 1H, J =4.4 Hz), 11.97 (s, 1H). $^{13}$C NMR (DMSO-d$_6$) δ 125.1, 132.7, 138.3, 144.7, 145.6, 152.9, 179.3. CIMS calcd for C$_7$H$_7$N$_5$O$_2$S 226 (MH$^+$), found 226.

Synthesis of 2-Vinyl Pyridine Compound (16)

A toluene solution (15 mL) of 2-chloro-3-nitropyridine 1 (417 mg, 2.63 mmol), Pd(PPh$_3$)$_4$ (32 mg, 0.026 mmol), triphenylphosphine (20 mg, 0.078 mmol) and vinyltributyltin (1.00 g, 3.16 mmol) was heated to reflux for 2 h. The reaction mixture was cooled to room temperature and then quenched with water (10 mL). The resulting mixture was extracted with EtOAc (3×30 mL). The combined organic layers were dried (Na$_2$SO$_4$) and filtered. The filtrates were concentrated in vacuo, and the residue was purified by silica gel chromatography (20–30% EtOAc/Hexanes) to provide 339 mg (86%) of the desired product 16 as a pale yellow oil.

$^1$H NMR (CDCl$_3$) δ 8.75 (dd, 1H, J=1.3 and 4.5 Hz), 8.16 (dd, 1H, J=1.3 and 8.1 Hz), 7.23–7.36 (m, 2H), 6.59 (dd, 1H, J=1.6 and 16.7 Hz), 5.70 (dd, 1H, J=1.6 and 10.4 Hz); LRMS m/e 151 (MH$^+$).

Synthesis of 2-Hemi-Acetal and 2-Carboxaldehyde Compounds (17 and 4) from 2-Vinyl Pyrdine Compound (16)

A methanol solution (20 mL) of 2-vinylpyridine 16 (800 mg, 5.33 mmol) was subjected to ozonolysis at −78° C. for 15 min. The reaction was quenched (at −78° C.) with Me$_2$S (2.2 mL), and the resulting reaction mixture was stirred overnight at room temperature. The solvent was evaporated, and the residue was subjected to short column (4" silica gel) chromatography, providing 850 mg (95%) of a mixture of products 17 and 4 (17/4=2:3).

The $^1$H NMR spectrum of aldehyde 4 matches the reported literature data (Sartorelli et al. *J. Med. Chem.* 1992, 35, 3672–3677).

$^1$H NMR of hemiacetal 17 (CDCl$_3$): δ 8.78 (m, 1H), 8.34 (m, 1H), 7.57 (m, 1H), 6.10 (d, 1H, J=8.7 Hz), 5.53 (m, 1H), 3.47 (s, 3H).

Synthesis of 2-Vinylester Compound 18

A mixture of 2-chloro-3-nitropyridine 1 (1.20 g, 7.6 mmol), methyl acrylate (1.31 g, 15.2 mmol), triethylamine (0.92 g, 9.1 mmol), triphenylphosphine (0.60 g, 2.28 mmol), Pd(OAc)$_2$ (0.17 g, 0.76 mmol), and 15 mL of DMF in a sealed tube was heated to 120° C. for 24 h. The reaction mixture was cooled to room temperature and then quenched with water (10 mL). The resulting mixture was extracted with EtOAc (3×30 mL). The combined organic layers were washed with brine, dried over $Na_2SO_4$ and filtered. The filtrates were concentrated and the residue was purified by silica gel chromatography (Hexane:EtOAc=4:1) to provide 0.80 g (51%) of the desired product 18 as yellow solid.

$^1$HNMR ($CDCl_3$) δ 8.85 (dd, 1H, J=1.5 and 4.5 Hz), 8.16 (dd, 1H, J=1.5 and 8.1 Hz), 7.49 (dd, 1H, J=4.8 and 8.4 Hz), 7.22 (d, 1H, J=15.3 Hz), 3.85 (s, 3H). LRMS m/e 209 ($MH^+$). HRMS calcd for $C_9H_8N_2O_4$ 208.0484, found 208.0484.

Synthesis of Hemi-Acetal and 2-Carboxaldehyde Compounds (17 and 4) from 2-Vinylester Compound 18

A solution of methanol-methyl chloride (12:1, 130 mL) of 18 (0.44 g, 5.33 mmol) was ozonolyzed at −78° C. and the reaction was monitored by TLC. After the reaction, the excess $O_3$ was removed by bubbling the reaction mixture with $O_2$ at −78 ° C. for 5 min. The reaction was then quenched (at −78° C.) with $Me_2S$ (5 mL), and the resulting reaction mixture was stirred overnight at room temperature. The solvent was evaporated, and the residue was purified by silica gel chromatography, (Hexanes:EtOAc=4:1 to Hexanes:EtOAc=1:1) to provide 0.286 g (83%) of a mixture of products 17 and 4 (17/4=1:2).

Synthesis of Hydrazone Compound 15 from a Mixture of Hemi-Acetal and Carboxaldehyde (17 and 4)

To an aqueous ethanol solution (10 mL of ethanol and 5 mL of water) of aldehyde 4 and hemiacetal 17 (850 mq, ~4.85 mmol) was added at room temperature conc. HCl (1 mL), followed by thiosemicarbazide (483 mg, 5.34 mmol). The reaction mixture was stirred at room temperature for 6 hr. At this point, the yellow solids were collected via filtration. The solids thus obtained were washed sequentially with water and ethanol three times, and then dried under high vacuum for 1 h, affording 1.0 g of the desired product 15 in 92% yield.

Synthesis of Compound 7 (3-AP) from Hydrazone (15)

Method 1

To a solution of $SnCl_2.2H_2O$ (2.256 g, 10 mmol) in 6 mL of ethanol was added nitro compound 15 (450 mg, 2.0 mmol). The reaction mixture was refluxed overnight under $N_2$ and filtered. The crude solid was dissolved in 30 mL of hot water and filtered. The filtrate was then adjusted to pH 7.5 with saturated $NaHCO_3$ solution and stirred at room temperature for 30 min, filtered, washed with $H_2O$, $C_2H_5OH$ and ether. The resulting yellow solid was further extracted with THF for several times. The combined THF extracts were evaporated off and the residue was dried in vacuo to provide 316 mg (81%) of 3-AP.

Method 2

A mixture of nitro compound 15 (450 mg, 2.0 mg) and $Na_2S$ (468 mg, 6 mmol) in $H_2O/C_2H_5OH$ (1:1, 20 mL) was stirred at room temperature for 18 h, concentrated. The residue was adjusted to pH 7.5 with 1N HCl solution, filtered, washed with $H_2O$, $C_2H_5OH$, $CH_2Cl_2$ and dried in vacuo to give 355 mq (91%) of 3-AP 7.

$^1$H NMR (DMSO-$d_6$) δ 6.43 (br, 2H), 7.07 (m, 2H), 7.80 (dd, 1H, J=1.2 and 4.2 Hz), 7.95 (br, 1H), 8.15 (br, 1H), 8.31 (s, 1H), 11.29 (s, 1H). $^{13}$C NMR(DMSO-$d_6$) δ 122.2, 124.4, 132.8, 137.1, 144.0, 149.2, 177.0. LRMS(FAB) m/e 196 ($MH^+$). HRMS calcd for $C_7H_9N_5S$ 196.0657, found 196.0657.

Synthesis of 2-Aminopyridine Derivative 20

Method 1

Reaction Performed in a Sealed Tube

A DMF (20 mL) suspension of 2-chloro-3-aminopyridine 19 (1.28 g, 10.0 mmol), styrene (5.72 mL, 50.0 mmol), sodium bicarbonate (1.68 g, 20.0 mmol), triphenylphosphine (1.31 g, 5.0 mmol) and $Pd(OAc)_2$ (0.12 g, 0.50 mmol) was heated at 130° C. for 24 hours in a sealed tube. At this point, the reaction mixture was cooled to room temperature, and quenched with saturated $NaHCO_3$ (10 mL) and water (10 mL). The reaction mixture was extracted with EtOAc (3×50 mL). The combined organic layers were washed with brine, dried over sodium sulfate and filtered. The filtrates were conc. in vacuo, the residue was chromatograhed (25% ethyl acetate in hexanes) to provide 1.47 g (75%) of the desired product 20.

Method 2

Reaction Performed Under 1 Atmosphere.

A DMF (150 mL) suspension of 2-chloro-3-aminopyridine 19 (20 g, 155.6 mmol), styrene (89 mL, 778 mmol), sodium bicarbonate (26 g, 311 mmol), triphenylphosphine (20 g, 78 mmol) and $Pd(OAc)_2$ (1.74 g, 7.8 mmol) was heated at 135° C. for 48 hours. At this point, the reaction mixture was cooled to room temperature, and then 100 mL of ethyl acetate was added. This mixture was filtered through celite and the filtrarte was concentrated in vacuo. The residue was chromatograhed (25% ethyl acetate in hexanes) to provide 22.7 g (74%) of the desired product 20 as a yellow solid.

Synthesis of Aldehyde 22 from 2-Aminopyridine Derivative 20

2-Aminopyridine derivative 20 (5.00 g, 25.51 mmol) was dissolved in warm tert-butanol (100 mL). To this warm solution (~40° C.) was added (t-Boc)$_2$O (6.68 g, 30.61 mmol). After stirring this solution at r.t. for a few hours, an additional amount of (t-Boc)$_2$O (2.78 g, 12.76 mmol) was added. The reaction was further stirred at r.t. for 15 hours. At this point, the milky suspension was subjected to solvent evaporation. After solvent removal, the resulting residue was taken up with (1:1) EtOAc/Et$_2$O (100 mL). The resulting solution was washed with brine. The organic layer was separated and saved. The aqueous layer was back extracted with the same mix-solvent (3×50 mL). The combined organic layers were dried and conc. in vacuo to provide ~10 g crude product 21 as light brown solid.

The crude N-Boc protected pyridine derivative 21 (~25.5 mmol) was dissolved in MeOH (120 mL) and dichloromethane (30 mL). The resulting solution was cooled to −78° C. and subjected to ozonalysis for ~45 minutes. The reaction was then quenched with Me$_2$S (8 mL) and stirred at r.t. overnight. Solvents were removed in vacuo, the residue was purified using silica gel chromatography (10–15% ethyl acetate in hexanes) to provide 5.23 g (92% for both steps) of the desired aldehyde 22 as white solid.

Synthesis of Compound 7 (3-AP) from Aldehyde 22

To a mixture of aldehyde 22 (1.468 g, 6.61 mmol) and thiosemicarbazide (662 mg, 7.27 mmol) in EtOH/H$_2$O (22.5 mL, 67% ethanol content) was added 3 mL of conc. HCl. The resulting solution was heated to reflux for 3 hours. The reaction was cooled to room temperature and filtered. The crude yellowish 3-AP—HCl salt was transferred to a flask. To this flask was added 40 mL hot water and 8 mL 10% NaHCO$_3$. The mixture was stirred at r.t. for 1 hour (at pH ~7.5). The solids were filtered and then rinsed with water (10 mL), EtOH (3 mL) and Et$_2$O (10 mL). The solids obtained were dried under high vacuum for a few hours to provide 1.195 g (93%) of the desired 3-AP 7.

Synthesis of Compound 10

Fuming sulfuric acid (500 g, 5.1 mol) was added slowly to 2,4-lutidine 8 (55 mL, 0.48 mol) and cooled in an ice bath with stirring. Potassium nitrate (87.5 g, 0.86 mol) was then added slowly. The reaction mixture was stirred at room temperature for 1 h and then allowed to warm to 110° C. for additional 7 h, cooled to room temperature and stirred overnight. The reaction mixture was poured onto ice (1.0 kg) and neutralized to pH 9 with solid NaOH, extracted with ether. The combined extracts were dried over anhydrous Na$_2$SO$_4$. The solvent was removed and the residue was distilled under reduced pressure to give 37.83 g (53%) of a mixture of 3-nitrolutidine 10 and 5-nitrolutidine 9. Further separation by distillation provided pure 3-nitrolutidine 10.

$^1$H NMR (CDCl$_3$) δ 2.35 (s, 3H), 2.57 (s, 3H), 7.13 (d, 1 H, J=4.8 Hz), 8.46 (d, 1 H, J=5.0 Hz).

Synthesis of Compound 11

A mixture of 3-nitrolutidine 10 (760 mg, 5 mmol) and selenium dioxide (555 mg, 5 mmol) in 15 mL of dioxane was refluxed for 14 h under N$_2$, additional SeO$_2$ (555 mg, 5 mmol) was added. The reaction mixture was refluxed for another 8 h, filtered through Celite. The solvent was removed under reduced pressure and the residue was isolated by flash chromatography on silica gel (hexane-EtOAc= 2:1) provided 357 mg (43%) of aldehyde 11.

$^1$H NMR (CDCl$_3$) δ 2.42 (s, 3H), 7.54 (d, 1H, J=4.9 Hz), 8.76 (d, 1H, J=4.9 Hz), 10.02 (s, 1H).

Synthesis of Hydrazone 27 from 2-Carboxaldhyde (11)

A mixture of aldehyde 11 (3.110 g, 18.73 mmol) and thiosemicarbazide (2.65 g, 29.08 mmol) in 70% ethanol (20 mL) was stirred at room temperature for 8 h, filtered, washed with H$_2$O, C$_2$H$_5$OH, ether and dried in vacuo to give 4.12 g (92%) of hydrazone 27.

$^1$H NMR (DMSO-d$_6$) δ 2.30 (s, 3H), 6.68 (br, 1H), 7.58 (d, 1H, J=5.1 Hz), 8.04 (s, 1H), 8.65 (d, 1H, J=4.8 Hz), 8.72 (br, 1H), 12.01 (s, 1H). $^{13}$C NMR (DMSO-d$_6$) 615.7, 126.5, 137.7, 139.6, 142.3, 144.9, 150.5, 178.8. LRMS m/e 240 (MH$^+$). HRMS calcd for C$_8$H$_9$N$_5$O$_2$S 240.0555, found 240.0557.

Synthesis of 2-0-Tf Compound 25

To 2-hydroxy-3-nitro-4-methyl-pyridine 24 (3.08 g, 20 mmol) and 4-dimethylaminopyridine (2.44 9, 20 mmol) dissolved in 5 mL of CH$_2$Cl$_2$ was slowly added triflic anhydride (5.7 g, 21 mmol) at 0° C. The reaction mixture was stirred at 0° C. overnight, then was diluted with 200 mL of CH$_2$Cl$_2$, followed by washing with water and brine, dried over MgSO$_4$. The crude compound after removing the solvent was chromatographed on a silica gel column, using 50% ethyl acetate in hexane to provide 4.95 g of the desired compound 25 (87%).

$^1$H NMR (DMSO-d$_6$) δ: 8.38 (d, 1H, J=5.1 Hz), 7.39 (d, 1H, J=5.1 Hz), 2.53 (s, 3H).

Synthesis of 2-Vinyl Pyridine Compound 26

A mixture of 2-hydroxy-3-nitro-4-methyl-pyridine triflate 25 (7.74 g, 27.06 mmol), tributyl vinyl tin (10.3 g, 32.47 mmol) and tetrakis(tripheylphosphine) palladium(0) (1.56 g, 1.35 mmol) in 100 mL of anhydrous toluene was heated to reflux for 3 h, then cooled to room temperature and quenched with 20 mL of brine. The mixture was then extracted with ethyl acetate (3×100 mL) and the combined organic layers were dried over MgSO$_4$. The crude product after evaporating the solvent was purified by silica gel column chromatography (hexane:ethyl acetate=5:1) to provide 2.82 g of the desired compound 26 (yield 70%).

$^1$H NMR (DMSO-d$_6$) δ: 8.51 (d, 1H, J=5.1 Hz), 7.13 (d, 1H, J=5.1 Hz), 6.66 (dd, 1H, J=10.5 and 12.3 Hz), 6.55 (d, 1H, J=1.8 Hz), 5.63 (dd, 1H, J=10.5 and 1.8 Hz), 2.32 (s, 3H). HRMS calcd for C$_8$H$_8$N$_2$O$_2$ 164.0586, found 164.0586.

Synthesis of 2-Carboxaldehyde 11 from 2-Vinyl Pyridine Compound 26

A solution of olefin 26 (4.03 g, 24.54 mmol) in 100 mL of methanol was ozonolyzed at −78° C. and the reaction was monitored by TLC. After the reaction, the excess O$_3$ was removed by bubbling the reaction mixture with O$_2$ at −78° C. for 5 min. The reaction was then quenched (at −78° C.) with Me$_2$S (10 mL), and the resulting reaction mixture was stirred overnight at room temperature. The solvent was evaporated, and the residue was purified by silica gel chromatography, (Hexanes:EtOAc=4:1 to Hexanes:EtOAc= 2:1) to provide 3.51 g (86%) of the aldehyde 11.

Synthesis of Compound 14 (3-AMP) from Hydrazone Compound 27

Method 1

To a solution of SnCl$_2$.2H$_2$O (2.256 g, 10 mmol) in 6 mL of ethanol was added nitro compound 27 (478 mg, 2 mmol). The reaction mixture was refluxed overnight under N$_2$, cooled and filtered. The solid was dissolved in 30 mL of hot water and filtered. The filtrate was then adjusted to pH 7.5 with saturated NaHCO$_3$ solution and stirred at room temperature for 30 min, filtered and washed with H$_2$O, C$_2$H$_5$OH and ether. The resulting yellow solid was then extracted several times with THF. The combined extracts were evaporated to dryness to provide 227 mg of 3-AMP 14. The first ethanol filtrate was evaporated off and the residue was adjusted to pH 8 with saturated NaHCO$_3$ solution, extracted twice with THF. The combined THF extracts were evaporated off and the residual solid was washed with H$_2$O, C$_2$H$_5$OH and ether. For the further purification, the solid was extracted with THF several times. The combined THF extracts were evaporated off to give another crop of 3-AMP (45 mg). Total yield: 65% (272 mg).

Method 2

A solution of nitro compound 27 (120 mg, 0.5 mmol) and Na$_2$S (117 mg, 1.5 mmol) in 6 mL of a 1:1 mixture of H$_2$O/C$_2$H$_5$OH was refluxed for 3 h under N$_2$. The solvent was concentrated and then adjusted to pH 7 with 1N HCl solution, filtered and washed with H$_2$O, C$_2$H$_5$OH, CH$_2$Cl$_2$ and dried in vacuo to provide 65 mg (62%) of 3-AMP 14.

$^1$H NMR (DMSO-d$_6$) δ 2.16 (s, 3H), 6.16 (br, 2H), 6.99 (d, 1H, J=4.4 Hz), 7.76 (d, 1H, J=4.4 Hz), 7.93 (br, 1H), 8.17

(br, 1H), 8.34 (s, 1H), 11.33 (s, 1H). FABMS calcd for $C_8H_{11}N_5S$ 210, found 210 (MH$^+$).

It is to be understood that the examples and embodiments described hereinabove are for the purposes of providing a description of the present invention by way of example and are not to be viewed as limiting the present invention in any way. Various modifications or changes that may be made to that described hereinabove by those of ordinary skill in the art are also contemplated by the present invention and are to be included within the spirit and purview of this application and the following claims.

We claim:

1. A method for producing a compound of the formula:

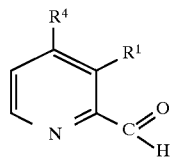

2-C where
$R^1$ is $NO_2$, $NH_2$, NHP, NPP', $N_3$ or $CO_2R^2$;
P and P' are protecting groups;
$R^2$ is Me, Et, Pr or I—Pr; and
$R^4$ is H or $CH_3$
comprising subjecting a compound of the formula:

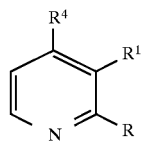

P where
R is Cl, Br, I, OMs, OTf or OTs;
$R^1$ is $NO_2$, $NH_2$, NHP, NPP', $N_3$ or $CO_2R^2$;
P and P' are protecting groups;
$R^2$ is Me, Et, Pr or I—Pr; and
$R^4$ is H or $CH_3$
to a vinylation reaction to produce a compound according to the formula:

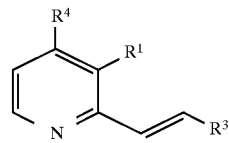

2-VP where
$R^1$ is $NO_2$, $NH_2$, NHP, NPP', $N_3$ or $CO_2R^2$;
P and P' are protecting groups;
$R^2$ is Me, Et, Pr or I—Pr; and
$R^3$ is H, $C_1$ to $C_{20}$ alkyl, aryl, substituted aryl or $CO_2R^2$; and
$R^4$ is H or $CH_3$;
and then subjecting compound 2-VP to ozonolysis to produce compound 2-C.

2. The method according to claim 1 wherein R is Cl, Br or I and $R^1$ is $NO_2$.
3. The method according to claim 1 wherein $R^3$ is H.
4. The method according to claim 1 wherein $R^3$ is a phenyl group.
5. The method according to claim 1 wherein $R^4$ is H.
6. The method according to claim 1 wherein $R^4$ is $CH_3$.
7. The method according to claim 1 wherein $R^1$ is $NO_2$.
8. The method according to claim 1 wherein $R^1$ is $NH_2$.
9. The method according to claim 1 wherein R is OMs, OTs or OTf.
10. A method of producing a compound of formula 4:

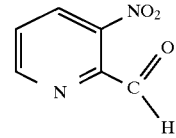

4 comprising reacting a compound according to a formula 3:

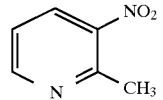

3 with dimethylformamidedialkylacetal to form a compound according to formula 3a:

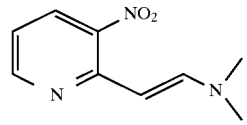

and then reacting said compound 3a with an oxidizing agent to form compound 4, said compound 4 being isolated in at least 75% yield from said compound 3.

11. The method according to claim 10 wherein said dimethylformamidedialkylacetal is dimethylformamidedimethylacetal.
12. The method according to claim 10 wherein said oxidizing agent is sodium periodate.

* * * * *